(12) United States Patent
Namba et al.

(10) Patent No.: US 7,196,339 B2
(45) Date of Patent: Mar. 27, 2007

(54) LIGHT-RECEIVING UNIT AND MEASURING APPARATUS INCLUDING THE SAME

(75) Inventors: Akihiro Namba, Tokyo (JP); Ryuji Sawada, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/290,225

(22) Filed: Nov. 30, 2005

(65) Prior Publication Data

US 2006/0109546 A1    May 25, 2006

Related U.S. Application Data

(63) Continuation of application No. PCT/JP04/07442, filed on May 25, 2004.

(30) Foreign Application Priority Data

May 30, 2003 (JP) .............................. 2003-155636

(51) Int. Cl.
*G01N 21/64* (2006.01)
(52) U.S. Cl. .................................. 250/458.1
(58) Field of Classification Search .............. 250/458.1
See application file for complete search history.

(56) References Cited

U.S. PATENT DOCUMENTS

2001/0054676 A1* 12/2001 Kawamura et al. ...... 250/208.1
2002/0121610 A1* 9/2002 Tewes et al. ............ 250/458.1
2003/0058442 A1* 3/2003 Garab et al. ................. 356/369
2005/0118640 A1* 6/2005 Kureshy et al. ............. 435/7.1

FOREIGN PATENT DOCUMENTS

| JP | 2002-139675 A | 5/2002 |
| JP | 2002-221663 A | 8/2002 |
| WO | WO 02/40953 A1 | 5/2002 |
| WO | WO 02/48963 A1 | 6/2002 |
| WO | WO 02097406 A1 * | 12/2002 |

* cited by examiner

*Primary Examiner*—Constantine Hannaher
(74) *Attorney, Agent, or Firm*—Scully, Scott, Murphy & Presser PC

(57) ABSTRACT

A measuring apparatus includes a confocal optical microscopy, an excitation light source unit that emits excitation light for generating fluorescence from a fluorescent material, and a light-receiving unit. The confocal optical microscope includes an excitation light input port for taking in excitation light from the excitation light source unit, and an output port for outputting fluorescence generated by the excitation light. The light-receiving unit includes an input portion for taking in signal light containing fluorescence from the confocal optical microscope. An input portion of the light-receiving unit is optically connected to the output port of the confocal optical microscope through an optical fiber.

24 Claims, 9 Drawing Sheets

LIGHT-RECEIVING UNIT AND MEASURING APPARATUS INCLUDING THE SAME

CROSS REFERENCE TO RELATED APPLICATIONS

This is a Continuation Application of PCT Application No. PCT/JP2004/007442, filed May 25, 2004, which was published under PCT Article 21(2) in Japanese.

This application is based upon and claims the benefit of priority from prior Japanese Patent Application No. 2003-155636, filed May 30, 2003, the entire contents of which are incorporated herein by reference.

BACKGROUND OF THE INVENTION

1. Field of the Invention

The present invention relates to a measuring apparatus for measuring light emitted from a specimen.

2. Description of the Related Art

As a measuring apparatus that analyzes statistical properties and molecular-level functions on a specific region in a specimen, for example, Japanese PCT National Publication No. 11-502608 discloses a method and apparatus that are based on a confocal optical microscope and obtain statistical properties such as the translational diffusion coefficients of fluorescent molecules, intermolecular interactions, and the like by applying laser light to a fluorescence-labeled specimen through the microscope objective lens, and analyzing fluorescence intensity fluctuations from fluorescent molecules in the specimen (performing fluorescence correlation spectroscopy).

As a description about a confocal optical microscope, for example, "Confocal Microscopy", T. Wilson (ed.), Academic press (London) is available. As a description mainly concerning a biological specimen, for example, "Handbook of Biological confocal Microscopy", J. B. Pawley (ed.), Plenum Press (New York) is available. With regard to a fluorescence correlation spectroscopy, there are available descriptions such as "Fluorescence correlation spectroscopy", R. Rigler, E. S. Elson (eds.), Springer (Berlin) and Masataka Kinjo, "Protein, nucleic acid and enzyme", (1999) Vol 44, No. 9, pp. 1431–1437.

According to fluorescence correlation spectroscopy, fluorescence-labeled protein or carrier particles are suspended in a solution within the field of view of a confocal scanning laser microscope, and an autocorrelation function is obtained by analyzing fluorescence intensity fluctuations based on the Brownian motion of the particles, thereby estimating the number, translational diffusion velocity, and the like of particles.

On the other hand, there is available confocal scanning laser microscope, which applies laser light to a fluorescence-labeled sample specimen by scanning the laser light, and generates a fluorescence microscope image of the specimen. A confocal scanning laser microscope is described in, for example, Jpn. Pat. Appln. KOKAI Publication No. 10-206742. There are also available descriptions made by Takahiro Oode et al. ("Optics", Vol. 18, Vol. 8, pp. 392–398), by Satoshi Kawata ("Optics", Vol. 18, Vol. 8, pp. 380–391), and the like.

According to U.S. Pat. No. 5,120,953, in a laser scanning confocal optical microscope, light from the laser source is guided to the optical fiber and to the microscope body, thereby irradiating a specimen surface with the light. A light signal from the specimen is guided to the optical fiber again through the microscope body and is received by the photo-detector connected to the optical fiber. That is, the light source and photodetector are optically connected to the microscope body through the optical fiber. According to U.S. Pat. No. 5,161,053, light from the light source of a confocal optical microscope is guided to the microscope body through an optical fiber, and a light signal from a specimen is optically branched to be guided to another optical fiber so as to be received by the photodetector optically connected thereto.

Japanese PCT National Publication No. 2001-505997 discloses a unit that is directly connected to a microscope to perform FCS measurement. A light source input/output port and a light signal output port are installed in this unit. Signal light output from the output port is received by a photodetector to perform FCS measurement.

In addition, Japanese PCT National Publication No. 2003-524180 discloses a unit that is connected to a microscope to perform FCS measurement. A light source body is incorporated in this unit. Light exits from the unit and is guided to the microscope, thereby irradiating the specimen with the light. A light signal emitted from the specimen is received in the unit through the microscope, and FCS measurement is performed.

BRIEF SUMMARY OF THE INVENTION

One aspect of the present invention is directed to a light-receiving unit that is connected to a confocal optical microscope to receive light emitted from a specimen. A light-receiving unit according to the present invention has an input portion to take in signal light output from the confocal optical microscope, and a light extracting unit that extracts specific light to be detected from the signal light taken in through the input portion.

Another aspect of the present invention is directed to a measuring apparatus for measuring light emitted from a specimen. A measuring apparatus according to the present invention comprises a light source unit that emits light for generating light from the specimen, a confocal optical microscope having a light input port to take in light for generating light from the specimen and an output port to output signal light, and a light-receiving unit connected to the confocal optical microscope, the light-receiving unit having an input portion to take in signal light output from the confocal optical microscope, and a light extracting unit that extracts specific light to be detected from the signal light taken in through the input portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

The embodiments of the present invention will be described below with reference to the views of the accompanying drawing.

First Embodiment

Figure 1:
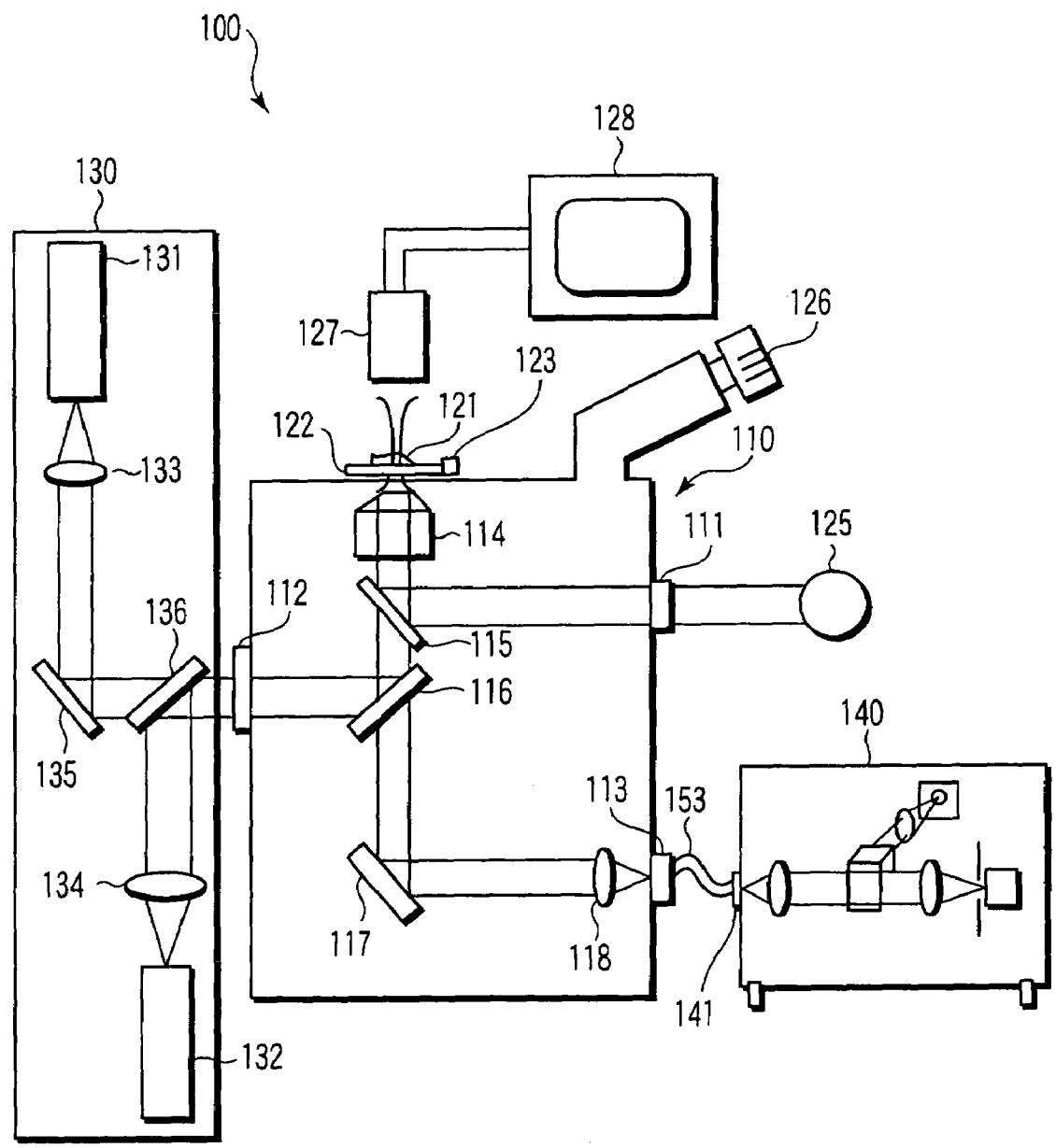
FIG. 1 shows the overall arrangement of a measuring apparatus that performs correlation analysis of fluorescence intensity fluctuations by using a confocal optical microscope according to the first embodiment of the present invention.
Figure 2:
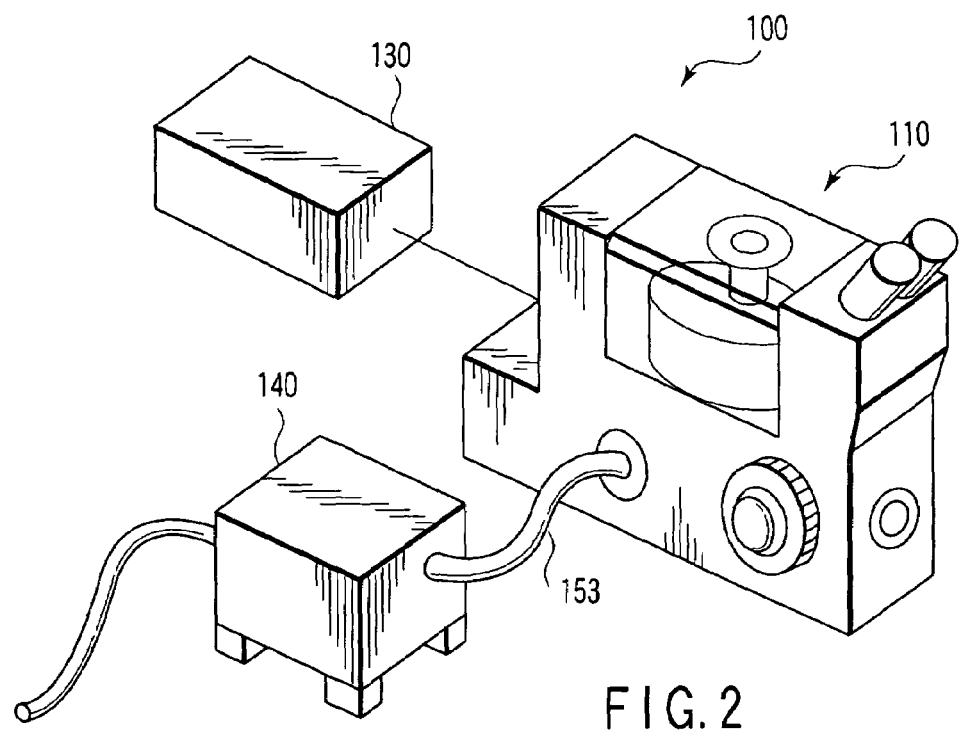
FIG. 2 schematically shows the outer appearance of the measuring apparatus shown in FIG. 1.
Figure 3:
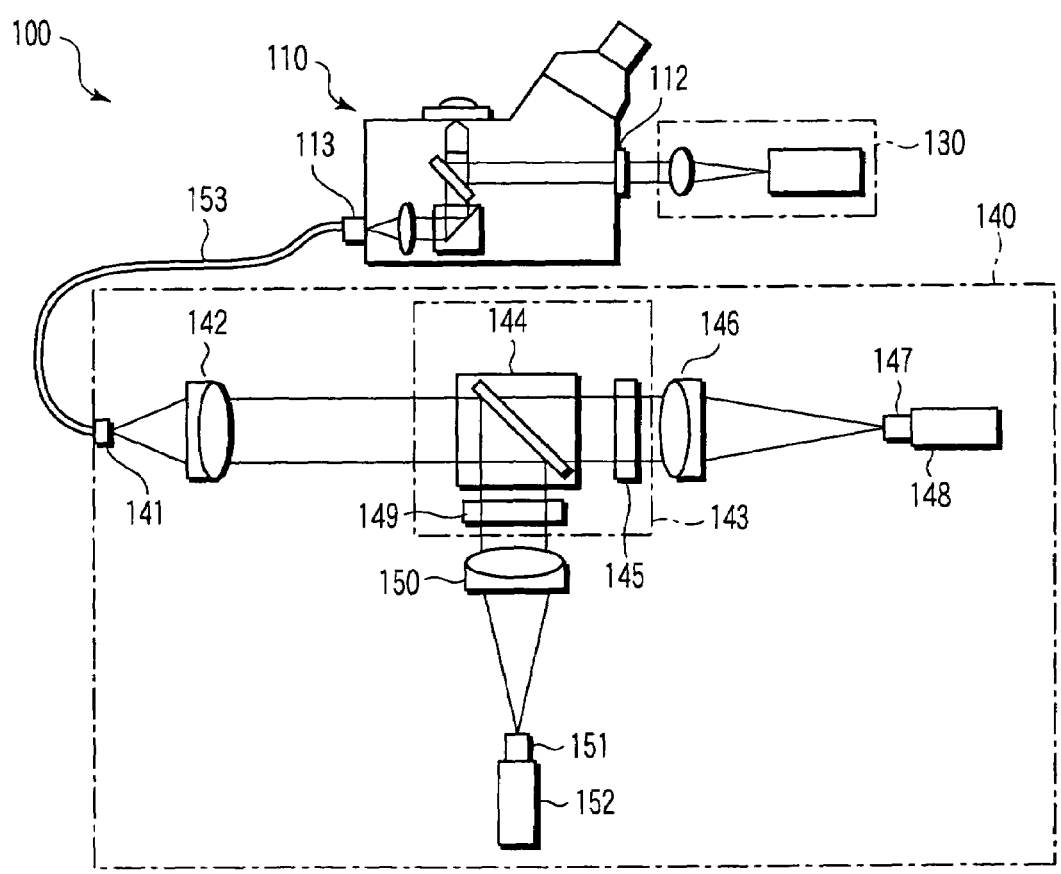
FIG. 3 shows the arrangement of a light-receiving unit shown in FIG. 1.
Figure 4:
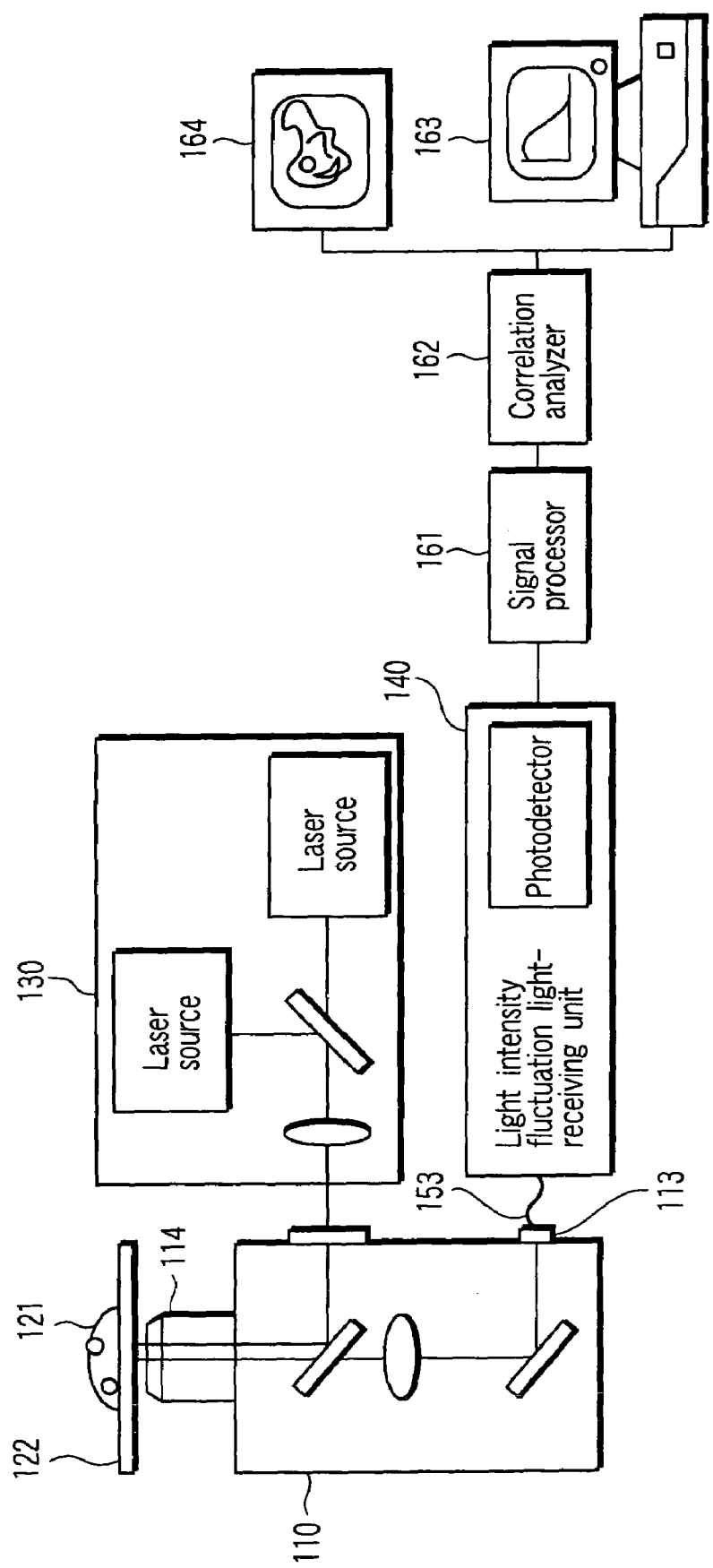
FIG. 4 shows the measuring apparatus and its signal processing system shown in FIG. 1.

This embodiment is directed to a measuring apparatus that performs correlation analysis on fluorescence intensity fluctuations (FCS) by using a confocal optical microscope. FIG. 1 shows the overall arrangement of a measuring apparatus that performs correlation analysis of fluorescence intensity fluctuations by using a confocal optical microscope according to the first embodiment of the present invention. FIG. 2 schematically shows the outer appearance of the measuring apparatus shown in FIG. 1. FIG. 3 shows the arrangement of the light-receiving unit shown in FIG. 1. FIG. 4 shows the measuring apparatus and its signal processing system shown in FIG. 1.

As shown in FIGS. 1 and 2, a measuring apparatus 100 of this embodiment includes a confocal optical microscope 110, an excitation light source unit 130 that emits excitation light for the emission of fluorescence from a fluorescent material, and a light-receiving unit 140.

As shown in FIG. 1, the confocal optical microscope 110 includes a sample stage 122 on which a specimen 121 is placed and two stepping motors 123 for moving the sample stage 122. The two stepping motors 123 are arranged so that their driving shafts are perpendicular to each other, and hence can move the sample stage 122 in two orthogonal directions, namely the x and y directions. The stepping motors 123 are controlled by a controller (not shown).

The measuring apparatus 100 further includes an illumination light source 125 for emitting illumination light for general optical observation. The confocal optical microscope 110 includes an illumination light input port 111 for taking in illumination light from the illumination light source 125, an excitation light input port 112 for taking in excitation light from the excitation light source unit 130, and an output port 113 for outputting fluorescence generated by excitation light.

The illumination light source 125 comprises, for example, a halogen lamp or metal halide lamp, although not limited to this.

The confocal optical microscope 110 includes an objective lens 114 placed below the sample stage 122, a dichroic mirror 115 that directs the illumination light taken in through the illumination light input port 111 to the objective lens 114, and an eyepiece lens 126 that allows an observer to visually observe the specimen 121.

The measuring apparatus 100 also includes a CCD camera 127 for acquiring an optical image of the specimen 121 and a TV monitor 128 that depicts (displays) the optical image acquired by the CCD camera 127.

The excitation light source unit 130 includes two laser sources 131 and 132, two lenses 133 and 134 that collimate light beams from the laser sources 131 and 132, a mirror 135 that directs a light beam from the lens 133 to the excitation light input port 112, and a dichroic mirror 136 that directs a light beam from the lens 134 to the excitation light input port 112.

As the laser sources 131 and 132 of the excitation light source unit 130, laser sources that emit light having a suitable wavelength in accordance with the optical properties of fluorescent material to be excited. Fluorescent materials are, for example, Rhodamine Green (RhG) and Cy5, although not limited to these. Accordingly, the laser source 131 is an argon laser, which emits light having a wavelength of 488 nm, for the excitation of Rhodamine Green (RhG), and the laser source 132 is a He—Ne laser, which emits light having a wavelength of 632.8 nm, for the excitation of Cy5.

The dichroic mirror 136 has the property of transmitting excitation light emitted from the laser source 131 and reflecting excitation light emitted from the laser source 132. The dichroic mirror 136 couples the excitation light from the laser source 131 and the excitation light from the laser source 132 and guides the coupled light to the excitation light input port 112.

The confocal optical microscope 110 includes a dichroic mirror 116 that reflects excitation light guided through the excitation light input port 112 to direct it to the objective lens 114 and transmits fluorescence emitted from the specimen 121, a mirror 117 that reflects a fluorescence beam from the dichroic mirror 116 to direct it to the output port 113, and a lens 118 that converges the fluorescence beam from the mirror 117.

As shown in detail in FIG. 3, the light-receiving unit 140 includes an input portion 141 for taking in signal light containing fluorescence from the confocal optical microscope 110, a lens 142 for collimating the signal light beam taken in through the input portion 141, a light extracting unit 143 that extracts fluorescence from signal light for each kind of dye, a lens 146 for converging one fluorescence beam, a photodetector 148 for detecting the fluorescence, a pinhole unit 147 placed in front of the photodetector 148, a lens 150 for converting the other fluorescence beam, a photodetector 152 for detecting the fluorescence, and a pinhole unit 151 placed in front of the photodetector 152.

The input portion 141 of the light-receiving unit 140 is optically connected to the output port 113 of the confocal optical microscope 110 with an optical fiber 153. The optical fiber 153 comprises a multi-mode optical fiber to guide light containing two kinds of fluorescence from the confocal optical microscope 110 to the light-receiving unit 140. The optical fiber 153 is, for example, a multi-mode optical fiber having a core diameter of 100 µm and an NA of 0.22, although not limited to this.

More specifically, the output port 113 is a port for the connection of, for example, a camera for photography, to which an optical fiber connection terminal (not shown) is attached. The optical fiber connection terminal is, for example, an FC connector, SC connector, ST connector, or the like, although not limited to this. A similar optical fiber connection terminal (not shown) is also attached to the input portion 141 of the light-receiving unit 140. The optical fiber 153 is connected to these optical fiber connection terminals.

The light extracting unit 143 includes a dichroic mirror 144 having the property of transmitting light in a wavelength band containing fluorescence from one kind of dye and reflecting light in a wavelength band containing fluorescence from the other kind of dye, a filter 145 having the property of selectively transmitting fluorescence containing that from one kind of dye, and a filter 149 having the property of selectively transmitting fluorescence containing that from the other kind of dye.

For example, in accordance with the above fluorescent materials, the dichroic mirror 144 transmits light in a wavelength band containing fluorescence emitted from Cy5 and reflects light in a wavelength band containing fluorescence emitted from Rhodamine Green (RhG). The filter 145 selectively transmits fluorescence emitted from Cy5 and selectively transmits fluorescence emitted from Rhodamine Green (RhG).

The pinhole unit 147 has a pinhole in a confocal position of the focal point of excitation light that generates fluorescence to be detected by the photodetector 148 located behind the pinhole unit 147. Likewise, the pinhole unit 151 has a pinhole in a confocal position of the focal point of excitation light that generates fluorescence to be detected by the photodetector 152 located behind the pinhole unit 151.

The photodetectors 148 and 152 output electrical signals corresponding to the intensity of incident light. The photodetectors 148 and 152 each are, for example, an avalanche photo diode (APD), although not limited to this. Alternatively, each photodetector may be a photomultiplier. The pinholes in the pinhole units 147 and 151 each have, for example, a diameter of 200 µm, although not limited to this. The objective lens 114 has, for example, an NA (Numerical Aperture) of about 1.0 to form a minute confocal area, although not limited to this. Thus it is obtained that a substantially columnar confocal area having a diameter of about 0.6 µm and a length of about 2 µm.

As shown in FIG. 4, the measuring apparatus 100 further includes a signal processor 161 that converts electrical signals output from the photodetectors 148 and 152 of the light-receiving unit 140 into on/off binary pulses by waveform-shaping the signals, a correlation analyzer 162 that gives an autocorrelation function by performing correlation calculation for the binary pulses output from the signal processor 161, and a computer 163 for obtaining changes in the translational diffusion velocity of a fluorescent material and the number of fluorescent molecules in a measurement area and the like from the autocorrelation function obtained by the correlation analyzer 162. The measuring apparatus 100 also includes a TV monitor 164 that displays the result obtained by the correlation analyzer 162.

In the measuring apparatus 100 according to this embodiment, fluorescence correlation spectrometry is performed in the following manner.

Referring to FIG. 1, an excitation light beam emitted from the laser source 131 is converted into a parallel light beam having a proper diameter by the lens 133. This light beam is reflected by the mirror 135, is transmitted through the dichroic mirror 136, and enters the confocal optical microscope 110 by spatial propagation through the excitation light input port 112. Note that this spatial propagation portion may be optical connection using a single-mode fiber.

An excitation light beam emitted from the laser source 132 is converted into a parallel light beam having a proper diameter by the lens 134. This light beam is reflected by the dichroic mirror 136 and enters the confocal optical microscope 110 through the excitation light input port 112.

The excitation light beam entering the confocal optical microscope 110 is reflected by the dichroic mirror 116, is transmitted through the dichroic mirror 115, and is converged by the objective lens 114. As described above, the objective lens 114 has a large numerical aperture of about 1.0, by which a substantially columnar confocal area having a diameter of about 0.6 µm and a length of about 2 µm is obtained.

A fluorescent material existing in this area is excited by excitation light to emit a fluorescence signal (photon pulses). Part of the fluorescence signal emitted from the fluorescent material reaches the objective lens 114 to become signal light containing a part of the reflected excitation light by the specimen 121. The signal light reaching the objective lens 114 is transmitted through the dichroic mirror 115 and dichroic mirror 116. This light is then reflected by the mirror 117 and converged by the lens 118. The signal light converged by the lens 118 enters the optical fiber 153 through the optical fiber connection terminal attached to the output port 113.

The signal light that enters the optical fiber 153 travels in the optical fiber 153 and exits from the input portion 141 of the light-receiving unit 140. As shown in FIG. 3, the signal light beam from the input portion 141 is converted into a parallel light beam having a shape of proper diameter with the lens 142, and is separated according to the spectral properties depending on the kinds of dye with the dichroic mirror 144. That is, fluorescence emitted from Cy5 is transmitted through the dichroic mirror 144, and fluorescence emitted from Rhodamine Green (RhG) is reflected by the dichroic mirror 144.

The filter 145 removes undesired spectral components from the light transmitted through the dichroic mirror 144. The resultant light is converged by the lens 146 and reaches the photodetector 148 through the pinhole unit 147 to be photoelectrically converted. Likewise, the filter 149 removes undesired spectral components from the light reflected by the dichroic mirror 144. The resultant light is converged by the lens 150 and reaches the photodetector 152 through the pinhole unit 151 to be photoelectrically converted.

Referring to FIG. 4, the electrical signals made by photoelectrical conversion with the photodetectors 148 and 152 are sent to the signal processor 161 to be converted into binary pulse signals. The binary pulse signals are sent to the correlation analyzer 162. The correlation analyzer 162 then obtains, for example, an autocorrelation function. The autocorrelation function is sent to the computer 163 to be used for the calculation of changes in the translational diffusion velocity of a fluorescent material and the number of fluorescent molecules in a measurement area and the like.

The correlation analyzer 162 may obtain a cross-correlation function for fluorescence intensity fluctuations with the two kinds of fluorescent molecules (Rhodamine Green and Cy5). Alternatively, the binary pulse signals output from the signal processor 161 may be directly input to the computer 163 without using the correlation analyzer 162, and the computer 163 may perform correlation analysis to obtain an autocorrelation function or cross-correlation function for fluorescence intensity fluctuations.

An autocorrelation function for fluorescence intensity fluctuations will be described below.

An autocorrelation function $R(\tau)$ for fluctuations in the intensity of fluorescence received by the photodetector from a fluorescent material is represented by $$R(\tau) = \int_0^T I(t)I(t+\tau)dt = \langle I(t)I(t+\tau) \rangle \quad (1)$$

where I is the intensity of fluorescence received by the photodetector from the fluorescent material, t is a time, and $\tau$ is a delay time. In addition, $\langle \; \rangle$ represents an ensemble average.

The autocorrelation function for fluorescence intensity fluctuations is normalized as follows:

$$G(\tau) = \frac{R(\tau)}{\langle I \rangle^2} = 1 + \frac{\langle I(t)I(t+\tau) \rangle}{\langle I \rangle^2} \quad (2)$$

$$G(0) \cong 1 + \frac{1}{N} \quad (3)$$

where $G(\tau)$ is the normalized autocorrelation function for fluorescence intensity fluctuations, and N is the average number of molecules existing in a confocal area. It is assumed that the existence probability of molecules existing in a confocal area complies with a Poisson distribution.

If incident light has spatially Gaussian distribution (argon laser, helium neon laser, or the like), the autocorrelation function $G(\tau)$ for fluorescence intensity fluctuations is given by $$G(\tau) = \frac{1}{N}\left(\frac{1}{1+4D\tau/\omega_1^2}\right)\left(\frac{1}{1+4D\tau/\omega_2^2}\right)^{1/2} + 1 \quad (4)$$

where D is the translational diffusion coefficients of fluorescent molecules, $\omega_1$ is the radius of the confocal area when it is approximated to a column, and $\omega_2$ is ½ the height of the area.

In this case, letting $\tau D$ be the diffusion time of the fluorescent material in a radial direction of the column, the following holds:

$$\tau_D = \frac{\omega_1^2}{4D} \quad (5)$$

When the size or the like of fluorescent molecules is to be estimated from the profile of the autocorrelation function for fluorescence intensity fluctuations, the autocorrelation function for fluorescence intensity fluctuations is divided by the square of the time average value of the fluorescence intensity fluctuations, and curve fitting is performed to obtain a diffusion time and a Y-axis intercept (the value on y-axis at the autocorrelation function intersects the y-axis). As a curve fitting method, the least square method may be used. For example, optimization may be performed by using the Levenberg Marquard method as one of the nonlinear least square methods (William H. Press et al., "Numerical Recipes in C", translated by Katsuichi Tankei, Gijutsu-Hyohron Co., Ltd, 1994).

As is obvious from equation (3), the value of the Y-axis intercept of the autocorrelation function for fluorescence intensity fluctuations corresponds to the average number of fluorescent molecules exiting in the confocal area (reference: "Single Molecule Detection in Solution", Ch. Zander, J. Enderlein, R. A. Keller (eds), WILEY-VCH, Germany).

In this embodiment, as shown in FIG. 2, the light-receiving unit 140 has a separable and independent structure from the confocal optical microscope 110, and is optically connected to the confocal optical microscope 110 with an optical fiber. The light-receiving unit comprises at least a condenser lens and a filter. The filter comprises a filter having a spectrum characteristic of selectively transmitting only a fluorescence wavelength from a specimen. As shown in FIG. 3, the light-receiving unit may comprise a photodetector in addition to the condenser lens and filter. This light intensity fluctuation unit can be easily connected and separated by using an optical connection terminal. When light intensity fluctuations are not to be measured, this unit may be kept separated at the optical connection terminal portion on the microscope body.

In this embodiment, the excitation light source unit 130 and the light-receiving unit 140 each have a separable unit structure that is independent on the confocal optical microscope 110. The excitation light source unit 130 is optically connected to the confocal optical microscope 110 through the excitation light input port 112. The light-receiving unit 140 is optically connected to the confocal optical microscope 110 through the output port 113.

Therefore, connecting the excitation light source unit 130, the light-receiving unit 140, and the like to the common confocal optical microscope 110 makes it possible to easily form an apparatus that performs correlation analysis of fluorescence intensity fluctuations.

Excitation light emitted from the excitation light source unit 130 is taken in the confocal optical microscope 110 through the excitation light input port 112, placed near the objective lens, without through the light-receiving unit 140. For this reason, the number of optical elements through which excitation light passes on the way is small, so that a decrease in excitation light intensity is suppressed. This allows excitation light to be efficiently applied to a specimen. In addition, the light passing through the light-receiving unit 140 is substantially exclusively the signal light emitted from the specimen. As a consequence, high S/N ratio of a signal is acquired with the apparatus.

Second Embodiment

This embodiment is directed to another measuring apparatus that performs correlation analysis of fluorescence intensity fluctuations by using a confocal optical microscope. The measuring apparatus of this embodiment differs from the measuring apparatus of the first embodiment in the layout of the photodetectors.

Figure 5:
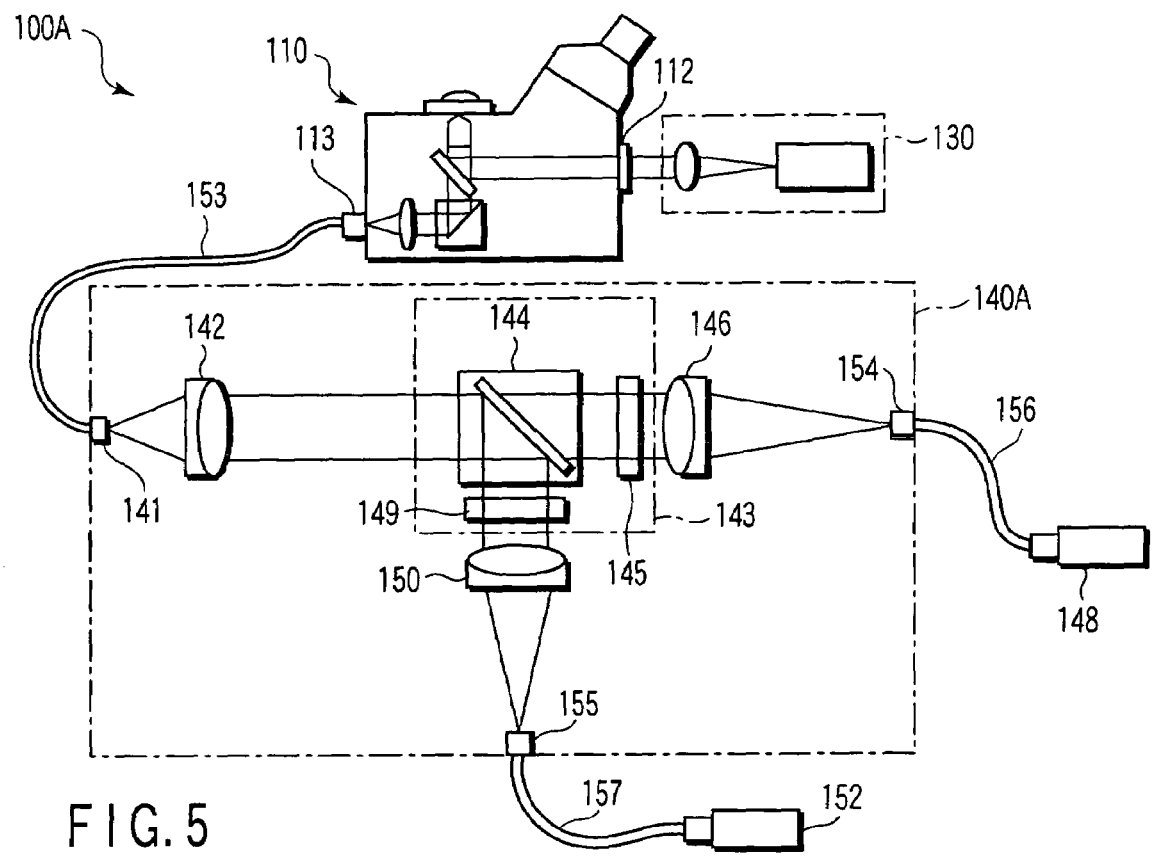
FIG. 5 schematically shows the arrangement of a measuring apparatus that performs correlation analysis of fluorescence intensity fluctuations according to the second embodiment of the present invention.

FIG. 5 schematically shows the arrangement of a measuring apparatus that performs correlation analysis of fluorescence intensity fluctuations according to the second embodiment of the present invention. The same reference numerals in FIG. 5 denote the same members as in FIG. 3, and a detailed description thereof will be omitted.

As shown in FIG. 5, in a measuring apparatus 100A according to this embodiment, a light-receiving unit 140A includes an input portion 141 for taking in signal light from a confocal optical microscope 110, a lens 142 for collimating a signal light beam, a light extracting unit 143 that extracts fluorescence from signal light for each kind, a lens 146 for converging one fluorescence beam, a fluorescence output portion 154 that outputs the fluorescence, a lens 150 for converging the other fluorescence beam, and a fluorescence output portion 155 for detecting the fluorescence.

As in the first embodiment, the input portion 141 of the light-receiving unit 140 is optically connected to an output port 113 of a confocal optical microscope 110 through a multi-mode optical fiber 153. The light extracting unit 143 includes a dichroic mirror 144 having the property of transmitting light in a wavelength band containing fluorescence from one kind of dye and reflecting light in a wavelength band containing fluorescence from the other kind of dye, a filter 145 having the property of selectively transmitting fluorescence from one kind of dye, and a filter 149 having the property of selectively transmitting fluorescence from the other kind of dye.

The fluorescence output portion 154 is optically connected to a photodetector 148 through, for example, a single-mode optical fiber 156, although not limited to this. The fluorescence output portion 155 is optically connected to the photodetector 148 through, for example, a single-mode optical fiber 157, although not limited to this.

The fluorescence output portion 154 has a pinhole in a confocal position of the focal point of excitation light that generates fluorescence to be detected by the photodetector 148. Likewise, the fluorescence output portion 155 has a pinhole in a confocal position of the focal point of excitation light that generates fluorescence to be detected by a photodetector 152. For example, the fluorescence output portions 154 and 155 may be optical fiber connection terminals, and the pinholes may be the end faces of the optical fibers 156 and 157 attached to them.

Measuring operation of the measuring apparatus 100A of this embodiment is the same as that of the measuring apparatus 100 of the first embodiment, and hence a description thereof will be omitted.

In the measuring apparatus 100A of this embodiment, since the photodetectors 148 and 152 are placed outside the light-receiving unit 140A, they can be placed in accordance with the placement of a signal processor, computer, and the like that are connected for the subsequent processing.

Third Embodiment

This embodiment is directed to another measuring apparatus that performs correlation analysis of fluorescence intensity fluctuations by using a confocal optical microscope. The measuring apparatus of this embodiment differs from the measuring apparatus of the first embodiment in optical connection between a confocal optical microscope and a light-receiving unit.

Figure 6:
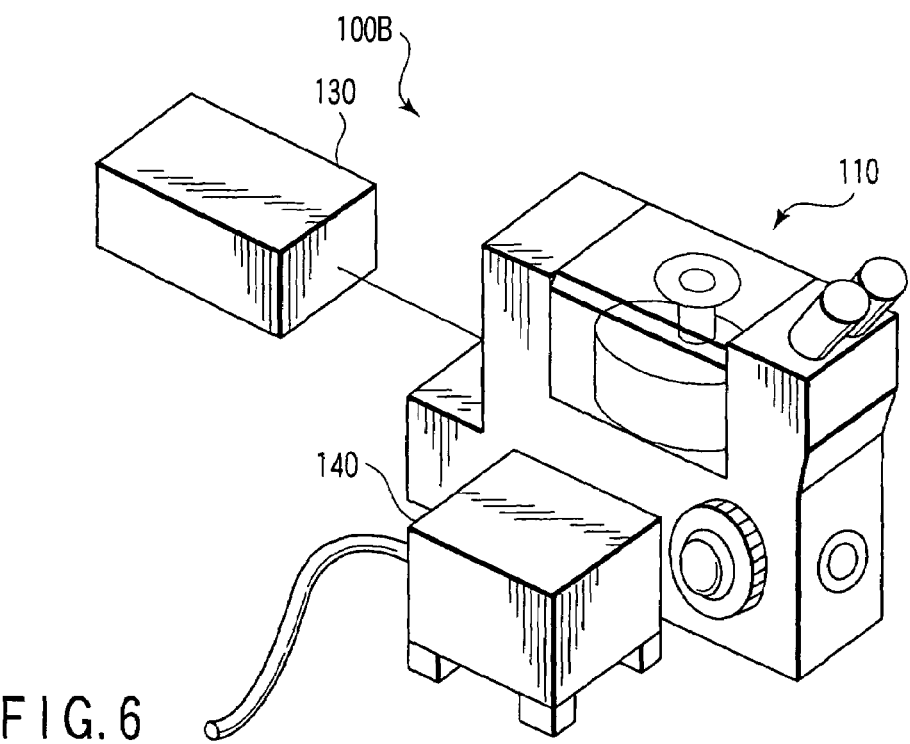
FIG. 6 schematically shows the arrangement of a measuring apparatus that performs correlation analysis of fluorescence intensity fluctuations according to the third embodiment of the present invention.

FIG. 6 schematically shows the arrangement of a measuring apparatus that performs correlation analysis of fluorescence intensity fluctuations according to the third embodiment of the present invention. The same reference numerals in FIG. 6 denote the same members as in FIG. 2, and a detailed description thereof will be omitted.

As shown in FIG. 6, in a measuring apparatus 100B of this embodiment, a confocal optical microscope 110 and a light-receiving unit 140 are simply connected to each other through a space without through any optical fiber. That is, although not shown in FIG. 6, an output port 113 (see FIG. 1 or 3) of the confocal optical microscope 110 is directly attached to an input portion 141 (see FIG. 1 or 3) of the light-receiving unit 140. Obviously, the output port 113 of the confocal optical microscope 110 may be connected to the input portion 141 of the light-receiving unit 140 through a member such as a lens barrel.

The measuring operation of the measuring apparatus 100B of this embodiment is the same as that of the measuring apparatus 100 of the first embodiment, and a description thereof will be omitted.

In the measuring apparatus 100B of this embodiment, since the confocal optical microscope 110 and the light-receiving unit 140 are simply connected to each other through a space, the fluorescence loss is small.

Fourth Embodiment

Figure 7:
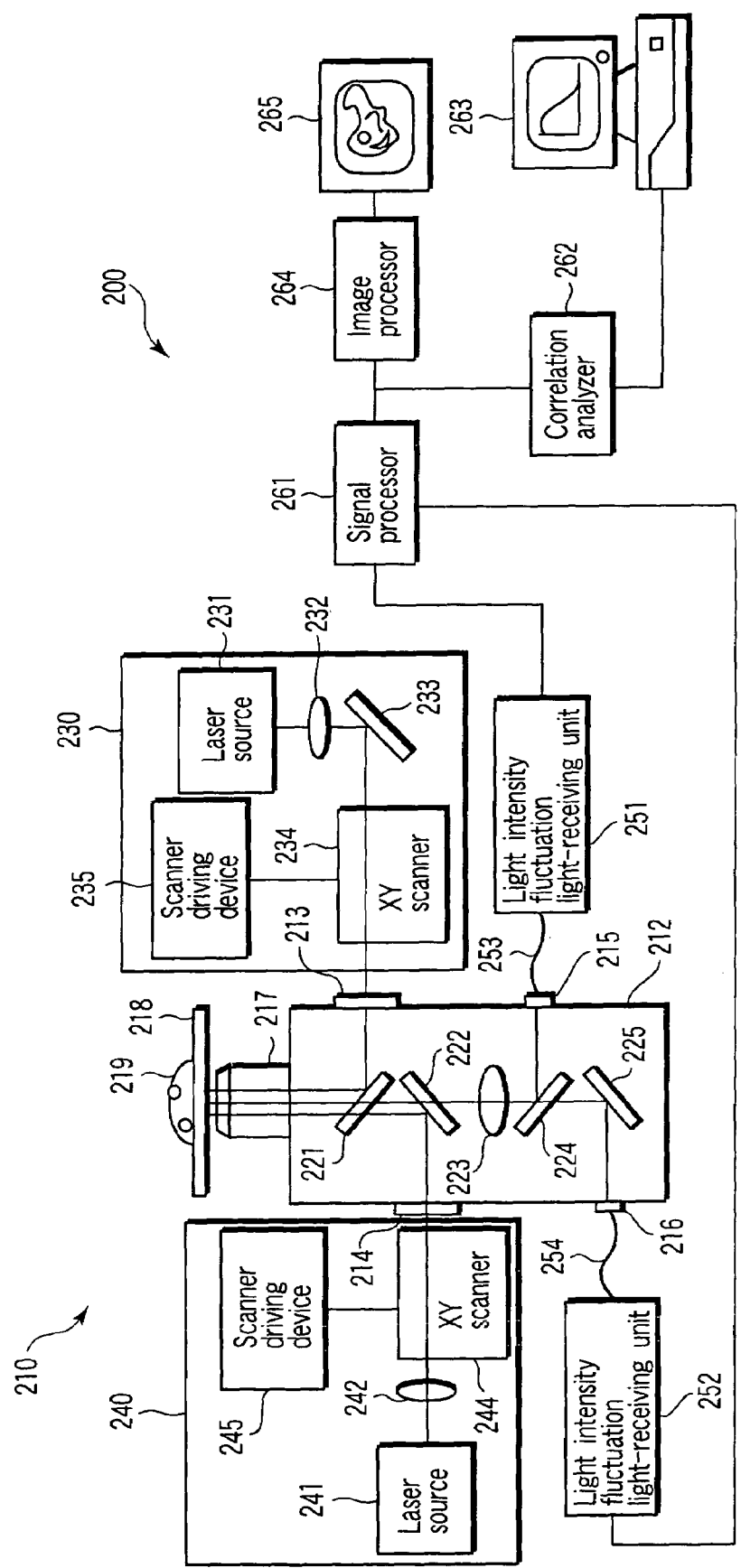
FIG. 7 shows the overall arrangement of a measuring apparatus that performs correlation analysis of fluorescence intensity fluctuations by using a confocal scanning laser microscope according to the fourth embodiment of the present invention.

This embodiment is directed to a measuring apparatus that performs correlation analysis of fluorescence intensity fluctuations by using a confocal scanning laser microscope. FIG. 7 shows the overall arrangement of a measuring apparatus that performs correlation analysis of fluorescence intensity fluctuations by using a confocal scanning laser microscope according to the fourth embodiment of the present invention.

As shown in FIG. 7, a measuring apparatus 200 of this embodiment includes a confocal scanning laser microscope 210. The confocal scanning laser microscope 210 includes a microscope body 212, an objective lens 217 attached to the microscope body 212, a sample stage 218 on which a specimen 219 is placed and that is placed above the objective lens 217, and two scanning light source units 230 and 240 that emit excitation light for the emission of fluorescence from a fluorescent material.

The microscope body 212 includes excitation light input ports 213 and 214 for taking in excitation light from the two scanning light source units 230 and 240, and two output ports 215 and 216 for outputting fluorescence generated by excitation light.

The scanning light source unit 230 includes a laser source 231, a lens 232 that collimates a light beam from the laser source 231, a mirror 233 that reflects the light beam from the lens 232, an XY scanner 234 that scans the light beam in two orthogonal directions (X and Y directions), and a scanner driving device 235 that drives the XY scanner 234.

Likewise, the scanning light source unit 240 includes a laser source 241, a lens 242 that collimates a light beam from the laser source 241, an XY scanner 244 that scans the light beam in two orthogonal directions (X and Y directions), and a scanner driving device 245 that drives the XY scanner 244.

The XY scanners 234 and 244 comprise, for example, two galvano scanner mirrors each of which can scan a light beam along one axis. The two galvano scanner mirrors are preferably arranged so that their scanning axes are perpendicular to each other. Alternatively, each scanner may comprise a polygon mirror or hologram scanner.

A light beam from the XY scanner 234 is taken in the microscope body 212 through the excitation light input port 213. A light beam from the XY scanner 244 is taken in the microscope body 212 through the excitation light input port 214.

As the laser sources 231 and 241, light sources that emit light having a suitable wavelength in accordance with the kind of fluorescent material to be excited are used as in the first embodiment. Fluorescent materials are, for example, Rhodamine Green (RhG) and Cy5, although not limited to these. Accordingly, the laser source 231 is an argon laser, which emits light having a wavelength of 488 nm, for the excitation of Rhodamine Green (RhG), and the laser source 241 is a He—Ne laser, which emits light having a wavelength of 632.8 nm, for the excitation of Cy5.

The microscope body 212 includes a dichroic mirror 221 that reflects excitation light introduced through the excitation light input port 213 to direct it to the objective lens 217, and transmits fluorescence emitted from the specimen 219, a dichroic mirror 222 that reflects excitation light introduced through the excitation light input port 214 to direct it to the objective lens 217, and transmits fluorescence emitted from the specimen 219, the lens 232 that converges the light transmitted through the dichroic mirror 222, a dichroic mirror 224 that transmits light in a wavelength band containing fluorescence from one kind of dye and reflects light in a wavelength band containing fluorescence from the other kind of dye, and a mirror 225 that directs the light transmitted through the dichroic mirror 224 to the output port 216.

The measuring apparatus 200 further includes two light-receiving units 251 and 252. The light-receiving units 251 and 252 are optically connected to the output ports 215 and 216 of the microscope body 212 through optical fibers 253 and 254, respectively. For example, the output ports 215 and 216 are ports for the connection of a camera for photography, and the optical fibers 253 and 254 are attached to the output ports 215 and 216 through optical fiber connection terminals.

The light-receiving units 251 and 252 respectively detect fluorescence emitted from the specimen 219 for each kind. The light-receiving units 251 and 252 each may have the same arrangement as that of the light-receiving unit 140 in the first embodiment. However, since each unit detects one kind of fluorescence, each unit may have filter and photodetector only for detecting one fluorescent dye.

For example, the light-receiving units 251 and 252 each may have an arrangement obtained by omitting the dichroic mirror 144, the filter 149, the lens 150, the pinhole unit 151, and the photodetector 152 from the light-receiving unit 140 shown in FIG. 3. Obviously, as a filter 145, a filter having characteristics suitable for the kind of fluorescence to be detected is used. In addition, a photodetector 148 may be an avalanche photo diode or photomultiplier as in the first embodiment.

For example, the dichroic mirror 224 transmits light in a wavelength band containing fluorescence emitted from Cy5 and reflects light in a wavelength band containing fluorescence emitted from Rhodamine Green (RhG). Accordingly, the light-receiving unit 252 detects fluorescence emitted from Cy5, and the light-receiving unit 251 detects fluorescence emitted from Rhodamine Green (RhG).

The measuring apparatus 200 further includes a signal processor 261 that converts electrical signals output from photodetectors in the light-receiving units 251 and 252 into on/off binary pulses by waveform-shaping the signals, a correlation analyzer 262 that obtains an autocorrelation function by performing correlation computation for the binary pulses output from the signal processor 261, and a computer 263 for obtaining changes in the translational diffusion velocity of a fluorescent material and the number of fluorescent molecules in a measurement area and the like from the autocorrelation function obtained by the correlation analyzer 262. The measuring apparatus 200 also includes an image processor 264 that performs image processing such as contrast improvement and edge enhancement with respect to the result obtained by the signal processor 261, and a TV monitor 265 that displays the image obtained by the image processor 264.

In the measuring apparatus 200 of this embodiment, an excitation light beam emitted from the laser source 231 is converted into a parallel light beam having a proper diameter by the lens 232. After this light beam is reflected by the mirror 233 and passes through the XY scanner 234, the light beam enters the microscope body 212 through the excitation light input port 213. The light beam is then reflected by the dichroic mirror 221 and converged by the objective lens 217 to form a light spot in the specimen 219. This light spot can be scanned in the X and Y directions by the XY scanner 234.

Part (i.e., signal light) of the reflected light and fluorescence from the specimen enters the objective lens 217, is transmitted through the two dichroic mirrors 221 and 222, and is reflected by the dichroic mirror 224 to be directed to the output port 215. The signal light enters the light-receiving unit 251 through the optical fiber 253 attached to the output port 215.

The light-receiving unit 251 removes undesired components from the signal light, and receives target fluorescence through the photodetector. The photodetector outputs an electrical signal reflecting the intensity of the received light.

The electrical signal output from the photodetector in the light-receiving unit 251 is subjected to image processing such as contrast improvement and edge enhancement by the image processor 264. The resultant signal is guided to the computer 263 to be formed into a two- or three-dimensional image of the specimen on the TV monitor 265.

An excitation light beam emitted from the laser source 241 is converted into a parallel light beam having a proper diameter by the lens 242, passes through the XY scanner 244, and enters microscope body 212 through the excitation light input port 214. The light beam is then reflected by the dichroic mirror 222, transmitted through the dichroic mirror 221, and converged by the objective lens 217, thereby forming a light spot in the specimen 219. This light spot is formed at a position different from that of the light spot of the excitation light from the laser source 231. In addition, this light spot can be scanned in the X and Y directions by the XY scanner 244.

Part (i.e., signal light) of the reflected light and fluorescence from the specimen enters the objective lens 217, is transmitted through the three dichroic mirrors 221, 222, and 224, and is reflected by the mirror 225 to be directed to the output port 216. The signal light passes through the optical fiber 254 attached to the output port 216 and enters the light-receiving unit 252.

The light-receiving unit 252 removes undesired components from signal light, and receives the target fluorescence through the photodetector. The photodetector outputs an electrical signal reflecting the intensity of the received light.

The electrical signal output from the photodetector in the light-receiving unit 252 is subjected to image processing such as contrast improvement and edge enhancement by the image processor 264. The resultant signal is guided to the computer 263 to be formed into a two- or three-dimensional image of the specimen on the TV monitor 265.

The measuring apparatus 200 of this embodiment can perform measurement with respect to a cross-correlation function for fluorescence intensity fluctuations as well as the autocorrelation function for fluorescence intensity fluctuations. The following information is obtained with respect to the molecules of fluorescent materials of two different kinds from the cross-correlation function for fluorescence intensity fluctuations.

At first, cross-correlation curve is obtained from dividing the cross-correlation function of fluorescence intensity fluctuations by the product of the time average values of fluctuations in the intensity of fluorescence received from the respective photodetectors. Next, curve fitting is performed for the curve. A value of a Y-axis intercept is obtained from the fitted curve. That is, the number of the clusters of molecules of two kinds of fluorescent materials is obtained according to equation (6) (Fluorescence Correlation Spectroscopy, R. Rigler and E. S. Elson eds. 15, Springer, Berline).

$$G(0) = \frac{N_{br}}{(N_r + N_{br})(N_b + N_{br})} \quad (6)$$

where G(0) is the value of the Y-axis intercept of the cross-correlation function for fluorescence intensity fluctuations based on the clusters of molecules of the two kinds of fluorescent materials (B and R), Nbr is the number of clusters of molecules of the two kinds of fluorescent materials (B and R) in the confocal area, Nr is the number of molecules of the fluorescent material R, and Nb is the number of molecules of the fluorescent material B.

Fifth Embodiment

This embodiment is directed to a measuring apparatus that performs time-resolved measurement of fluorescence by using a confocal optical microscope. The arrangement of the measuring apparatus of this embodiment is almost the same as that of the measuring apparatus according to the second embodiment.

Figure 8:
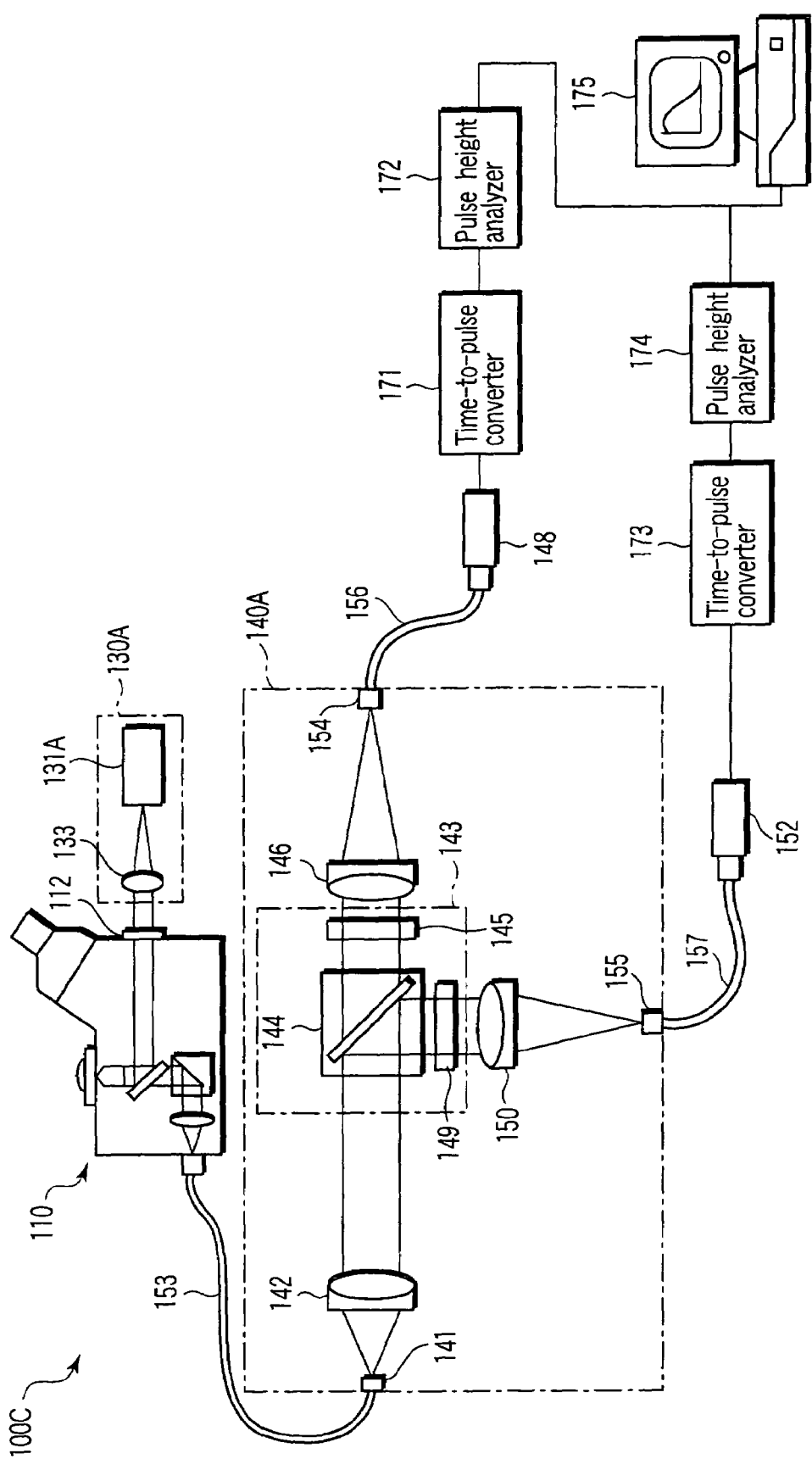
FIG. 8 schematically shows the arrangement of a measuring apparatus that performs time-resolved measurement of fluorescence according to the fifth embodiment of the present invention.

FIG. 8 schematically shows the arrangement of a measuring apparatus that performs time-resolved measurement of fluorescence according to the fifth embodiment of the present invention. The same reference numerals in FIG. 8 denote the same members as in FIG. 5, and a detailed description thereof will be omitted.

As shown in FIG. 8, a measuring apparatus 100C of this embodiment comprises a pulse excitation light source unit 130A in place of the excitation light source unit 130 of the measuring apparatus 100A of the second embodiment. Other arrangements are the same as those in the second embodiment.

The pulse excitation light source unit 130A comprises a pulse laser source 131A and lens 133. The pulse laser source 131A comprises, for example, a CW mode-locked argon-ion laser with a wavelength of 514.5 nm, an average output of 100 mW, and a pulse width of 200 psec, although not limited to this.

Although FIG. 8 representatively shows one pair of the pulse laser source 131A and the lens 133, the pulse excitation light source unit 130A may comprise a plurality of pairs of pulse laser sources and lenses as with the case of the excitation light source unit 130 shown in FIG. 1.

In the measuring apparatus 100C of this embodiment, a time-to-pulse height converter (time-to-amplitude converter) 171 and a pulse height analyzer (multi-channel analyzer) 172 are sequentially connected to a photodetector 148, and a computer 175 is connected to the pulse height analyzer 172. In addition, a time-to-pulse height converter 173 and a pulse height analyzer 174 are connected to the photodetector 152, and the computer 175 is connected to the pulse height analyzer 174.

The specimen is a medium including a cell, a DNA having a fluorescent material labeled with a base, and a carrier material.

Pulse light emitted from the pulse laser source 131A is taken in a confocal optical microscope 110 through an excitation light input port 112, and is applied to a specimen containing a fluorescent material on the specimen stage. Signal light emitted from the fluorescent material in the specimen reaches a light-receiving unit 140A through an optical fiber 153 coupled to the confocal optical microscope 110. The light-receiving unit 140A extracts specific fluorescence from the signal light and outputs it. The fluorescence output from the light-receiving unit 140A is detected by photodetectors 148 and 152 connected to the light-receiving unit 140A through optical fibers 156 and 157, respectively. The photodetectors 148 and 152 detect photons of the fluorescence and generate photoelectronic pulses. The detection pulse signals are guided to the time-to-pulse height converters 171 and 173 to serve as stop signals for the time-to-pulse height converters 171 and 173. On the other hand, signals synchronized with the emission of light from the pulse laser source 131A are sent to the time-to-pulse height converters 171 and 173. The signals are used as start signals for the time-to-pulse height converters 171 and 173. The time-to-pulse height converters 171 and 173 each output a voltage pulse signal proportional to the time difference between the two output signals, i.e., the start and stop signals. The output pulse signals are guided to the pulse height analyzers 172 and 174 to be converted into the output pulse height. The resultant signals are sent to the computer 175 and stored in a memory (not shown) in the computer. The fluorescence life time of fluorescent molecules in the specimen can be obtained by graphing the relationship between the heights of the output signal pulses stored in the memory and the time.

Figure 9A:
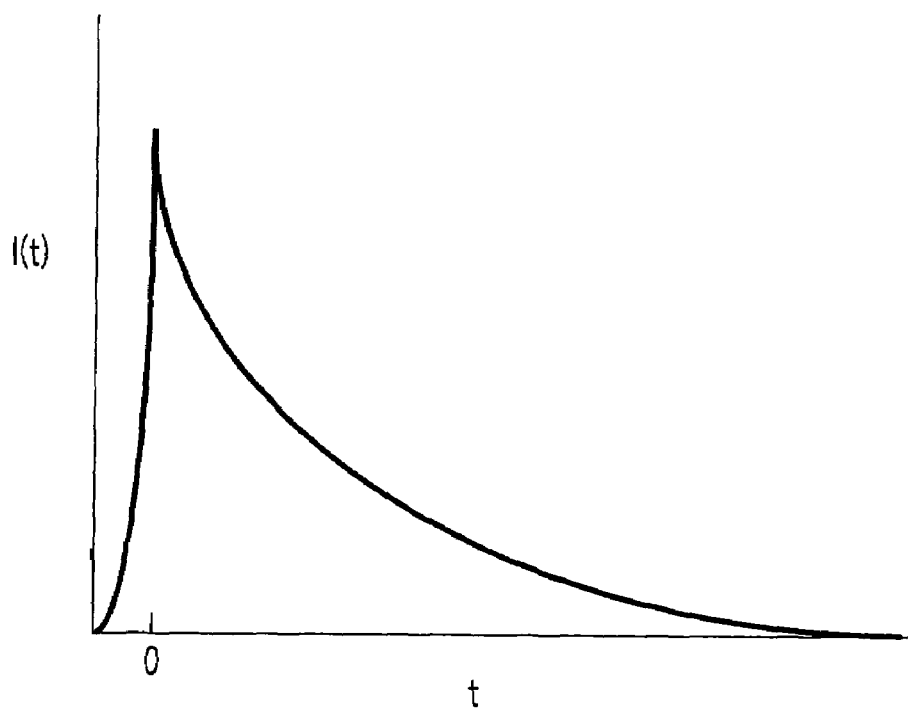
FIG. 9A shows a measurement result on a specimen with a long fluorescence life time, which is obtained by the measuring apparatus shown in FIG. 8, and a transient change in the intensity of fluorescence emitted from fluorescent molecules in the specimen.
Figure 9B:
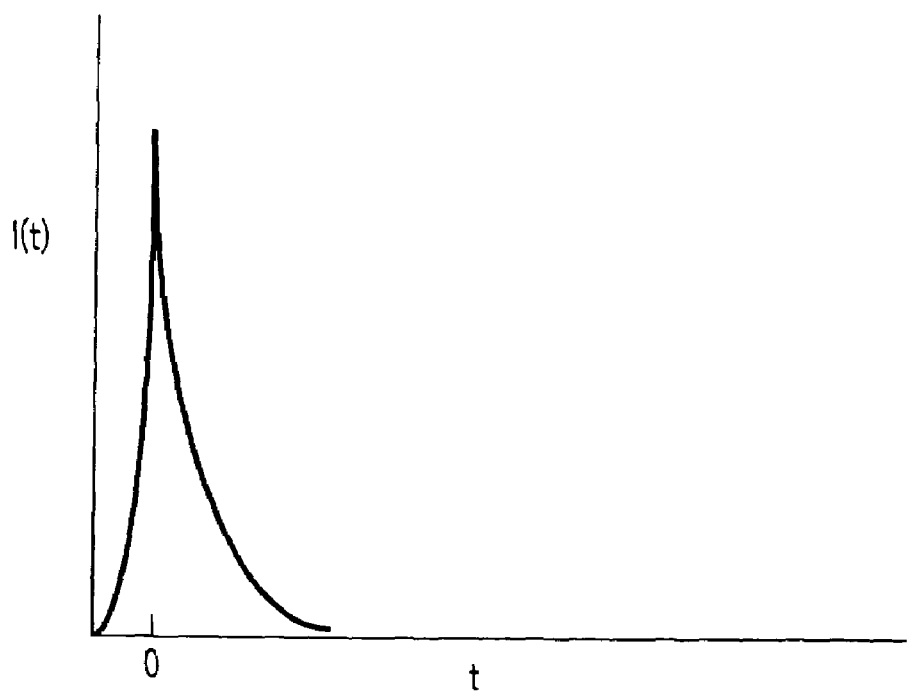
FIG. 9B shows a measurement result on a specimen with a short fluorescence life time, which is obtained by the measuring apparatus shown in FIG. 8, and a transient change in the intensity of fluorescence emitted from fluorescent molecules in the specimen.

FIGS. 9A and 9B each show the measurement result obtained by the measuring apparatus shown in FIG. 8 and indicate a temporal change in the intensity of fluorescence emitted from fluorescent molecules in a specimen. FIG. 9A shows the measurement result on a specimen with a long fluorescence life time. FIG. 9B shows the measurement result on a specimen with a short fluorescence life time.

In this embodiment, pulse light emitted from the pulse excitation light source unit 130A is taken in the confocal optical microscope 110 through the excitation light input port 112, which is placed near the objective lens, without through the light-receiving unit 140A. For this reason, the number of optical elements through which pulse light passes on the way is small, so that a decrease in pulse light intensity is suppressed. This allows pulse light to be efficiently applied to a specimen. In addition, the light passing through the light-receiving unit 140A is substantially only the signal light emitted from the specimen. As a consequence, measurement can be done with the high S/N ratio of a signal.

The arrangement of the measuring apparatus of this embodiment can be properly changed as needed. For example, the pulse laser source 131A may be changed to a CW mode-locked dye laser source, and measurement may be performed upon changing the wavelength of pulse light. As in the first embodiment, the photodetectors 148 and 152 may be arranged in the light-receiving unit. That is, the light-receiving unit 140A, the optical fibers 156 and 157, and the photodetectors 148 and 152 may be changed to the light-receiving unit 140 in the first embodiment.

Sixth Embodiment

This embodiment is directed to a measuring apparatus that measures a change in the polarization characteristics of fluorescence emitted from a fluorescent material in a specimen such as fluorescence depolarization, the degree of polarization, and the like by using a confocal optical microscope. The arrangement of a measuring apparatus according to this embodiment is similar to that of the measuring apparatus according to the second embodiment.

Figure 10:
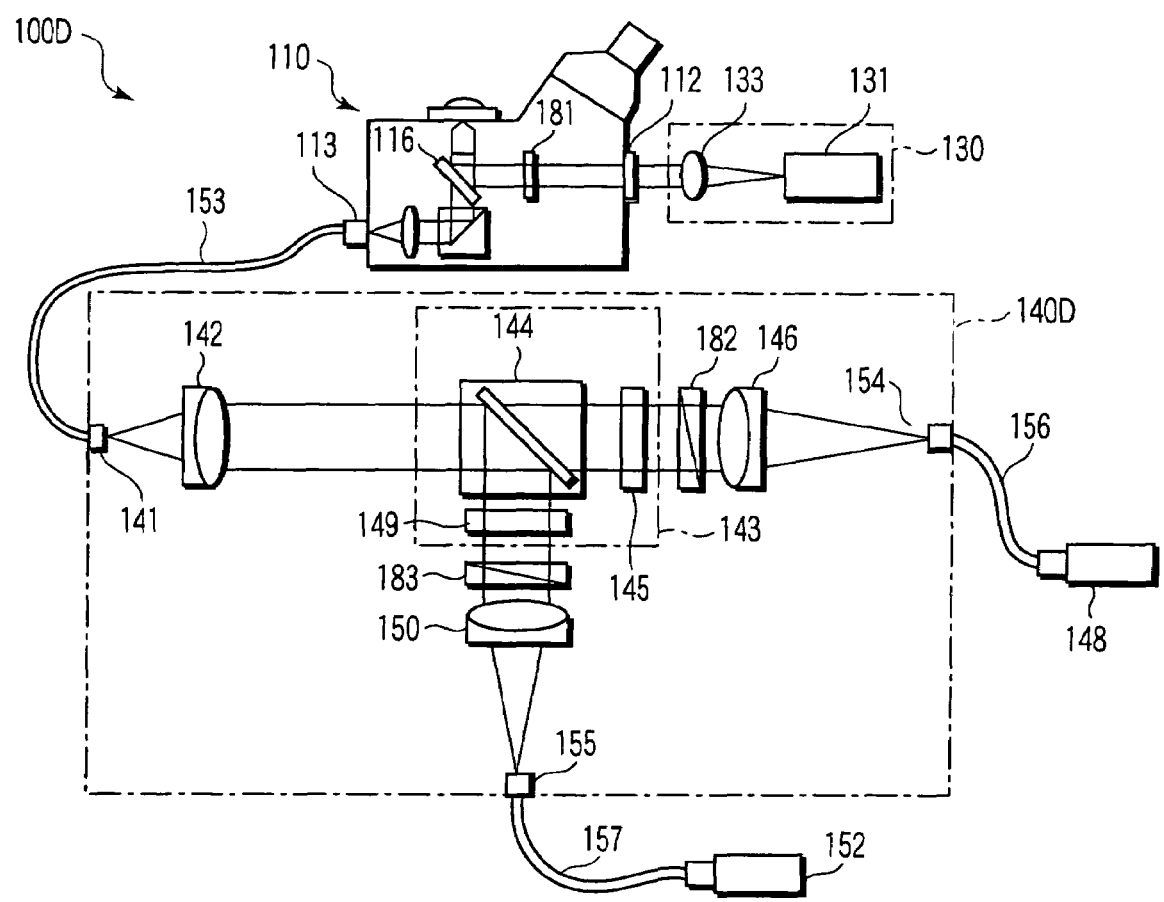
FIG. 10 schematically shows the arrangement of a measuring apparatus that performs measurement associated with the polarization of fluorescence according to the sixth embodiment of the present invention.

FIG. 10 schematically shows the arrangement of a measuring apparatus that performs measurement associated with the polarization of fluorescence according to the sixth embodiment of the present invention. The same reference numerals in FIG. 10 denote the same members as in FIG. 5, and a detailed description thereof will be omitted.

As shown in FIG. 10 in a measuring apparatus 100D according to this embodiment, a confocal optical microscope 110 comprises a polarizing element 181 that is placed on the optical path of excitation light from an excitation light source unit 130 and selectively transmits a specific polarized component. A light-receiving unit 140D has an arrangement obtained by adding polarizing elements 182 and 183 that selectively transmit specific polarized components to the light-receiving unit 140A of the measuring apparatus 100A of the second embodiment. Other arrangements are the same as those of the second embodiment.

More specifically, the confocal optical microscope 110 comprises the polarizing element 181 on an optical path between an excitation light input port 112 and a dichroic mirror 116. In addition to the arrangement of the light-receiving unit 140A, the light-receiving unit 140D includes the polarizing element 182 placed between a filter 145 and a lens 146 and the polarizing element 183 placed between a filter 149 and a lens 150. The transmission axes of the polarizing elements 182 and 183 are orthogonal to the transmission axis of the polarizing element 181. That is, the polarizing directions of light transmitted through the polarizing elements 182 and 183 are orthogonal to the polarizing direction of light transmitted through the polarizing element 181.

The polarizing elements 181, 182, and 183 each comprise, for example, a polarizing plate and, more preferably, may comprise a polarizing element with a high extinction ratio, e.g., a Glan Thompson Prism, although not limited to this.

The excitation light source unit 130 includes a continuous wave laser source 131. The laser source 131 comprises, for example, an argon laser with a wavelength of 488 nm and an output of 10 mW, although not limited to this.

Although FIG. 10 representatively shows one laser source 131, the excitation light source unit 130 may includes a plurality of laser sources.

Excitation light emitted from the laser source 131 is taken in the confocal optical microscope 110 through the excitation light input port 112. A specific polarized component is extracted by the polarizing element 181 and is applied to a specimen containing a fluorescent material on the specimen stage. Signal light emitted from the fluorescent material in the specimen reaches the light-receiving unit 140A through an optical fiber 153 coupled to the confocal optical microscope 110. The light-receiving unit 140D causes a light extracting unit 143 to extract specific fluorescence from the signal light. The light-receiving unit 140D further causes the polarizing elements 182 and 183 to extract and output a polarized component that is orthogonal to a polarized component of excitation light applied to the specimen. The fluorescence of the specific polarized components output from the light-receiving unit 140A is detected by photodetectors 148 and 152 connected to the light-receiving unit 140A through optical fibers 156 and 157, respectively.

In this embodiment, linearly-polarized excitation light is applied to a specimen containing fluorescent molecules, and the two photodetectors 148 and 152 detect linearly-polarized light orthogonal to the excitation light from fluorescence emitted from the specimen. This makes it possible to measure the anisotropy and polarization degree of fluorescence of fluorescent molecules in the specimen. For example, a rotational diffusion coefficient reflecting the velocity of the rotational Brownian motion of fluorescent molecules and the like can be obtained. The measuring apparatus 100D of this embodiment uses an objective lens (NA: 0.9) with a high numerical aperture, and hence can check the polarization characteristics of an intracellular DNA labeled with a fluorochrome molecule and tissue such as a cell membrane. In addition, the swinging motion of an LB (Langmuir-Blodgett) film and the like can be measured.

In addition, an antigen-antibody reaction can be measured by detecting the intensity of scattered light emitted from a specimen. For example, a latex particle suspension (mass concentration: 0.005%) sensitized with an Alpha Fetoprotein (AFP) antibody with a diameter of 0.2 µm is used as a specimen, and a test substance such as blood is injected into the specimen to cause an antigen-antibody reaction. In this case, if an AFP antibody is contained in the test substance, latex particles coagulate due to the antigen-antibody reaction. If latex particles are monodispersed, the scattered light from them has no anisotropy, and the particles emit light having a polarized component in the same direction as the polarizing direction of incident light as scattered light. As the latex particles coagulate, however, scattered light have anisotropy. This makes it possible to clearly discriminate an unreacted dispersed state. Therefore, an antigen-antibody reaction can be measured with high sensitivity.

In this embodiment as well, excitation light emitted from the excitation light source unit 130 is taken in the confocal optical microscope 110 through the excitation light input port 112 placed near the objective lens without through the light-receiving unit 140D. For this reason, the number of optical elements through which excitation light passes on the way is small, so that a decrease in excitation light intensity is suppressed. This allows excitation light to be efficiently applied to a specimen. In addition, the light passing through the light-receiving unit 140D is substantially only the signal light emitted from the specimen. As a consequence, measurement can be done with the high S/N ratio of a signal.

The arrangement of the measuring apparatus according to this embodiment may be properly changed, as needed. For example, all or some of the polarizing elements 181, 182, and 183 may have circular outer shapes and may be placed rotatably around a central axis. The rotation of each polarizing element may be controlled manually or by being motor-driven in accordance with the rotation of a stepping motor by connecting the stepping motor to the rotating shaft of the polarizing element. By making each polarizing element rotatable in this manner, the polarizing direction of incident light can be freely changed in accordance with a specimen. Accordingly, the polarizing directions of the two polarizing elements 182 and 183 in the light-receiving unit 140D are changed to allow measurement under optimal conditions in accordance with the specimen.

The laser source 131 may comprise a laser source that emits linearly polarized light. In this case, the polarizing element 181 in the confocal optical microscope 110 can be omitted.

Seventh Embodiment

This embodiment is directed to another measuring apparatus that performs measurement associated with the polarization of fluorescence by using a confocal optical microscope. The arrangement of the measuring apparatus of this embodiment is almost the same as that of the measuring apparatus according to the sixth embodiment.

Figure 11:
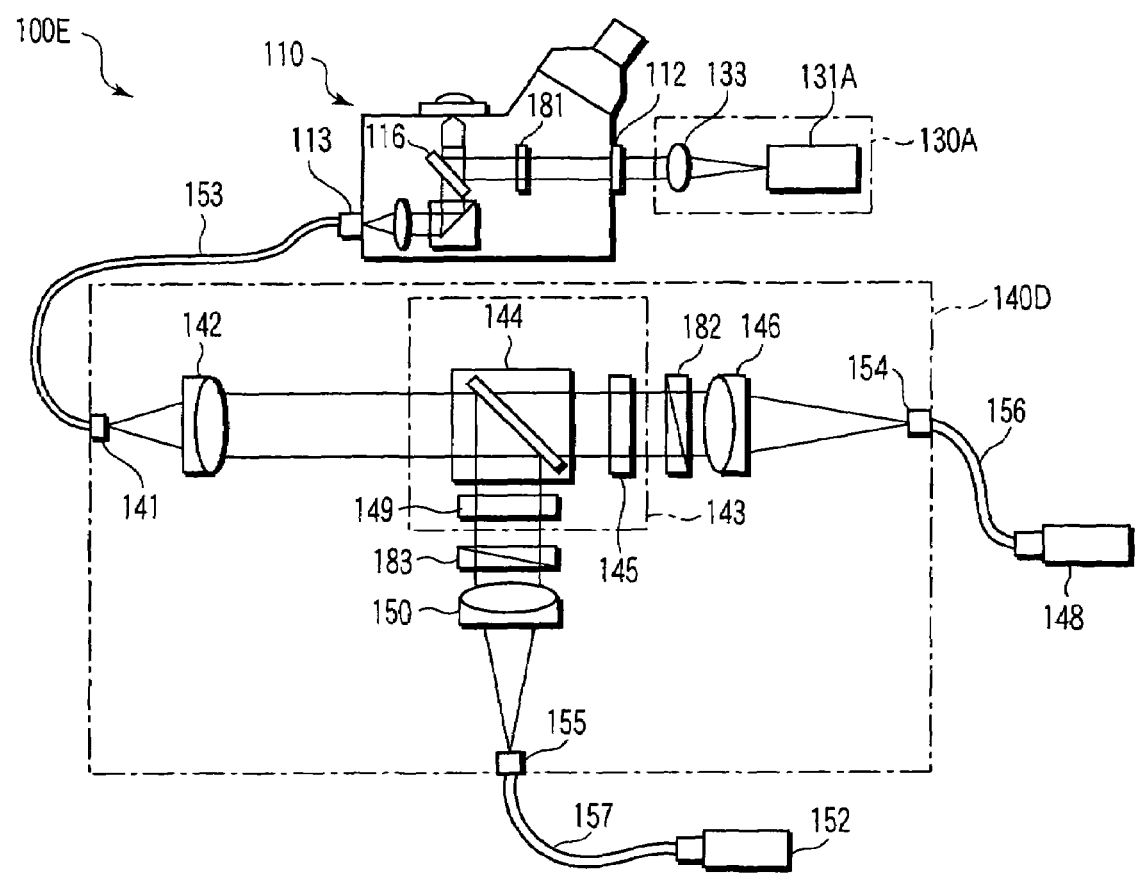
FIG. 11 schematically shows the arrangement of a measuring apparatus that performs measurement associated with the polarization of fluorescence according to the seventh embodiment of the present invention.

FIG. 11 schematically shows the arrangement of a measuring apparatus that performs measurement associated with the polarization of fluorescence according to the seventh embodiment of the present invention. The same reference numerals in FIG. 11 denote the same members as in FIG. 10.

As shown in FIG. 11, a measuring apparatus 100E of this embodiment comprises a pulse excitation light source unit 130A described in the fifth embodiment in place of the excitation light source unit 130 in the sixth embodiment. Other arrangements are the same as those of the sixth embodiment. That is, the measuring apparatus 100E of this embodiment has an arrangement obtained by replacing the excitation light source unit 130 of the measuring apparatus 100D of the sixth embodiment with the pulse excitation light source unit 130A of the measuring apparatus 100C of the fifth embodiment.

In this embodiment, ultra-short pulse light emitted from a pulse laser source 131A is taken in a confocal optical microscope 110, and is linearly polarized by a polarizing element 181 in the confocal optical microscope 110. The resultant light is applied to a specimen containing a fluorescent material on a specimen stage. At this time, the fluorescent material in the specimen is excited by absorbing only a polarized component of the applied pulse light that coincides with the direction of the transition moment of the fluorescent material, so as to emit fluorescence. The fluorescence emitted from the fluorescent material has a polarized component in a direction coinciding with the direction of the transition moment of the fluorescent material. Exciting the fluorescent material by using polarized ultra-short pulse light in this manner and performing time-resolved measurement with respect to the polarized component of the fluorescence emitted from the fluorescent material make it possible to obtain a temporal change in the molecular orientation of the fluorescent material.

Other Embodiments

For example, the binding and dissociation of proteins can be known by obtaining FRET (Fluorescence Resonance Energy Transfer) by using the measuring apparatus in FIG. 8. For example, quantitative measurement of a calcium ion concentration in a cell can be done. In addition, the distances between various regions of a biopolymer, the tertiary and quaternary structures of a biopolymer, its dynamic changes can be measured.

When a calcium ion ($Ca^{2+}$) binds with Calmodulin in a cell, the Calmodulin is activated and undergoes a structural change. The structural change of the Calmodulin can be known by labeling different regions of the Calmodulin with different fluorescent materials, exciting one fluorescent material, and measuring fluorescence from the other fluorescent material, which is obtained by fluorescence resonance energy transfer. The phosphorylation of a protein can be measured by labeling the two terminals of the protein with two different kinds of fluorescent proteins, e.g., CFP (cyan fluorescent protein) and YFP (yellow fluorescent protein). As a protein phosphorylates, the structure of the protein changes. With this structural change, when the two fluorescent proteins approach very close to each other (about 10 nm or less), FRET occurs. The phosphorylation of the protein can be clarified by measuring this FRET.

For example, the measuring apparatus shown in FIG. 8 may be applied to the measurement of phosphorescence as well as fluorescence. In this case, a light extracting unit 143 is applied to the extraction of phosphorescence.

In addition, for example, the measuring apparatus in FIG. 8 may be applied to the measurement of a luminescence phenomenon such as chemiluminescence or bioluminescence. In this case, the light extracting unit 143 is applied to the extraction of light of chemiluminescence or bioluminescence. Since no light source is required, the light source may be removed or the power switch of the light source may be turned off. For example, consider a case where enzyme immunoassay of an Alpha Fetoprotein (AFP) as a major cancer marker is performed by chemiluminescence using the measuring apparatus in FIG. 8 (from which the light source is removed). First of all, fine glass particles with diameters of about 1 to 10 μm are sensitized with an anti-AFP antibody, and the resultant structure is then labeled with enzyme alkaline phosphatase. The resultant structure is suspended in a buffer solution and preserved in a specimen vessel. A test substance such as blood is added to this solution to cause an antigen-antibody reaction at room temperature. At this time, fine glass particles that do not contribute to the reaction are removed by washing, and the chemiluminescence AMPPD (2-dioxetane disodium salt) is added to the remaining solution. At this time, the AMPPD reacts with enzyme alkaline phosphatase to cause chemiluminescence. The luminescence intensity of this chemiluminescence is measured by a photodetector and introduced to the computer to analyze the light intensity. This makes it possible to determine the AFP concentration in the test substance.

The embodiments of the present invention have been described with reference to the views of the accompanying drawing. However, the present invention is not limited to the embodiments, and various modifications and changes thereof can be made within the spirit and scope of the invention.

For example, when one kind of fluorescent material is to be measured, a simple arrangement in which the multi-mode optical fiber 153 in FIG. 5 is directly connected to one photodetector 148 or 152 may be used.

In addition, the present invention may be applied to measurements other than those in the above embodiments. For example, the present invention may be applied to arbitrary microoptical measurements for the measurement of various kinds of optical characteristics (polarization, scattering, electrochemical luminescence, resonance energy transfer, plasmon resonance, and the like) only within a specific region or area of a specimen as a measurement target.

The present invention is not limited to the above embodiments and incorporates measurement signal processing units and measurement device systems to be described in the following items.

1. A measurement signal processing unit characterized by having:

a connection portion that can be connected to a measuring device having an external output portion that externally outputs a measurement signal;

a signal propagation mechanism having a propagation means corresponding to an output signal (light, acoustic wave, current, or the like) from the measuring device; and an element that receives a signal propagating from the signal propagation mechanism and acquires a specific parameter contained in the signal.

2. A measurement signal processing unit according to item 1, wherein the element that acquires a parameter has a data conversion means for converting to a computable electrical signal.

3. A measurement signal processing unit according to item 2, characterized by having an external output portion that outputs post-computation data to an external device that has a data visualizing means for visualizing post-computation data in an expressive form that allows visual recognition (numerals, graphs, images, characters, symbols, or the like).

4. A measurement signal processing unit according to item 3, characterized in that the external output portion for post-computation data includes a propagation means and a connection portion.

5. A measurement processing unit according to item 1, wherein the connection portion includes a multi-mode waveguide means.

6. A measurement processing unit according to any one of items 1 to 5, wherein the computation unit is configured to function in accordance with software having an algorithm for analyzing fluorescence intensity fluctuations.

7. A measuring device system comprising:
the measurement processing unit described in item 3, and
a measuring device that is connected to the measurement processing unit,
wherein the measuring device has a measurement signal processing unit characterized by having a data visualization means for visualizing post-computation data in an expressive expression that allows visual recognition.

8. A measuring device system comprising:
the measurement processing unit described in item 1; and
a measuring device connected to the measurement processing unit,
wherein the measuring device has a propagation means for propagating a signal source (light, acoustic wave, current, or the like) necessary for measurement and an external input portion that can input a propagation signal from outside the device to the propagation means, and
a connection portion that can be connected to the external input portion and a signal source introducing unit that introduces a propagation signal necessary for computation by the measurement processing unit through the connection portion.

9. A measuring device system according to item 8, wherein the connection portion of the signal source introducing unit includes a single-mode waveguide means.

10. A measuring device system according to item 9, wherein the connection portion of the measurement processing unit includes a multi-mode waveguide means.

11. A measuring device system according to any one of items 7 to 10, wherein the measuring device is one of a microscope, an endoscope, and an analyzer.

12. A measuring device system according to any one of items 7 to 10, wherein the measuring device has a measuring means using a light signal.

13. A measuring device system according to item 12, wherein the computing unit functions in accordance with software having an algorithm for analyzing light intensity fluctuations.

As has been described above, the present invention can be a measurement processing unit that can be applied to a measuring device using another signal source such as an ultrasonic microscope or scanning tunneling microscope. In addition, the present invention can be a measuring device system that allows a special signal source to be separately connected. Furthermore, the present invention can be a system that can also be connected to an endoscope and analyzer in addition to a microscope.

What is claimed is:

1. A measuring apparatus for measuring light emitted from a specimen, comprising:
a light source unit that emits light for generating light from the specimen, the light source unit inluding a lens that collimates light to be projected from the light source unit;
a confocal optical microscope having a light input port to take in light for generating light from the specimen and an output port to output signal light; and
a light-receiving unit connected to the confocal optical microscope, the light-receiving unit having an input portion to take in signal light output from the confocal optical microscope, and a light extracting unit that extracts specific light to be detected from the signal light taken in through the input portion;
wherein the confocal optical microscope has an objective lens opposed to a specimen, the input portion of the light-receiving unit is optically connected to the output port of the confocal optical microscope, and the output port is located farther from the objective lens than the light input port.

2. A measuring apparatus according to claim 1, wherein the light-receiving unit is configured to be allowed to separate from the confocal optical microscope.

3. A measuring apparatus according to claim 1, wherein the light-receiving unit is connected to the confocal optical microscope for correlation analysis of a fluorescence intensity fluctuation, the signal light output from the confocal optical microscope contains fluorescence, and the light extracting unit extracts specific fluorescence to be detected from the signal light taken in through the input portion.

4. A measuring apparatus according to claim 3, wherein the light-receiving unit further has a photodetector to detect fluorescence, the photodetector has a pinhole placed in front of a light-receiving surface of the photodetector, and the pinhole is in a confocal position of a focal point of excitation light that generates fluorescence.

5. A measuring apparatus according to claim 4, wherein the light source unit emits a plurality of kinds of excitation light, the confocal optical microscope outputs signal light containing a plurality of kinds of fluorescence, the light-receiving unit has detectors corresponding in number to kinds of fluorescence, the light extracting unit separates and extracts fluorescence according to the kinds, and the detectors detect corresponding kinds of fluorescence.

6. A measuring apparatus according to claim 5, wherein the output port of the confocal optical microscope and the input portion of the light-receiving unit are optically connected to each other through a multi-mode light guide.

7. A measuring apparatus according to claim 4, wherein the input portion of the light-receiving unit is directly attached to the output port of the confocal optical microscope.

8. A measuring apparatus according to claim 4, wherein the output port of the confocal optical microscope and the input portion of the light-receiving unit are optically connected to each other through a light guide.

9. A measuring apparatus according to claim 3, wherein the light-receiving unit further has a fluorescence output portion to output fluorescence, the fluorescence output portion includes a pinhole, and the pinhole is in a confocal position of a focal point of excitation light to generate fluorescence, and further comprising a photodetector to detect fluorescence, the photodetector being optically connected to the fluorescence output portion.

10. A measuring apparatus according to claim 9, wherein the light source unit emits a plurality of kinds of excitation light, the confocal optical microscope outputs signal light containing a plurality of kinds of fluorescence, the light-receiving unit has fluorescence output portions corresponding in number to kinds of fluorescence, the light extracting unit separates and extracts fluorescence according to the kinds, and the fluorescence output portions output corresponding kinds of fluorescence.

11. A measuring apparatus according to claim 1, wherein the light for generating light from the specimen is converged to a point by the objective lens, and the light-receiving unit has a pinhole in a confocal position of the focal point of light for generating light from the specimen.

12. A measuring apparatus according to claim 11, wherein the light-receiving unit further has a photodetector to detect light passing through the pinhole.

13. A measuring apparatus according to claim 11, wherein the light-receiving unit further has a light output portion to output light passing through the pinhole, and the light output portion is optically connected to the photodetector.

14. A measuring apparatus according to claim 11, wherein the light-receiving unit further has a polarizing element that is placed between the input portion and the pinhole and selectively transmits a specific polarized component.

15. A measuring apparatus according to claim 1, wherein the light for generating light from the specimen is converged to a point by the objective lens, signal light output from the confocal optical microscope contains light of a plurality of wavelengths, the light extracting unit separates and extracts light according to kinds, the light-receiving unit has pinholes corresponding in number to kinds of wavelengths of light extracted by the light extracting unit, and all the pinholes are in a confocal position of the focal point of light for generating light from the specimen.

16. A measuring apparatus according to claim 15, wherein the light-receiving unit further has a plurality of photodetectors to detect light passing through the pinholes.

17. A measuring apparatus according to claim 15, wherein the light-receiving unit further has a plurality of light output portions to output light passing through the respective pinholes, and the light output portions are optically connected to the photodetectors, respectively.

18. A measuring apparatus according to claim 15, wherein the light-receiving unit further has a plurality of polarizing elements that are respectively placed between the light extracting unit and the pinholes and selectively transmit specific polarized components.

19. A measuring apparatus according to claim 1, wherein the light source emits light for generating light from the specimen as a light pulse.

20. A measuring apparatus according to claim 1, wherein the signal light contains scattered light emitted from the specimen, and at least one of measurement of a scattered light intensity, correlation analysis of a scattered light intensity fluctuation, and measurement of a polarized component of a scattered light intensity is performed.

21. A measuring apparatus according to claim 1, wherein the signal light contains fluorescence emitted from the specimen, and the light-receiving unit is applied to at least one of measurement of a fluorescence intensity, correlation analysis of a fluorescence intensity fluctuation, and measurement of a polarized component of a fluorescence intensity.

22. A measuring apparatus according to claim 1, wherein one of measurement of chemiluminescence, measurement of bioluminescence, and measurement of phosphorescence is performed.

23. A measuring apparatus according to claim 1, wherein the output port of the confocal microscope and the input portion of the light-receiving unit are optically connected to each other through an optical fiber.

24. A measuring apparatus for measuring light emitted from a specimen, comprising:
    a light source unit that emits light for generating light from the specimen, the light source unit including a lens that collimates light to be projected from the light source unit;
    a confocal optical microscope having a light input port to take in light for generating light from the specimen and an output port to output signal light; and
    a light-receiving unit connected to the confocal optical microscope, the light-receiving unit having input means for taking in signal light output from the confocal optical microscope, and light extracting means for extracting specific light to be detected from the signal light taken in through the input means;
    wherein the confocal optical microscope has an objective lens opposed to a specimen, the input portion of the light-receiving unit is optically connected to the output port of the confocal optical microscope, and the output port is located farther from the objective lens than the light input port.

* * * * *